United States Patent
Formica

(10) Patent No.: US 9,757,179 B2
(45) Date of Patent: Sep. 12, 2017

(54) CRYO-SURGICAL SYSTEMS AND METHODS OF USING THE SAME

(71) Applicant: ORASURE TECHNOLOGIES, INC., Bethlehem, PA (US)

(72) Inventor: Philip Michael Formica, Center Valley, PA (US)

(73) Assignee: ORASURE TECHNOLOGIES, INC., Bethlehem, PA (US)

( * ) Notice: Subject to any disclaimer, the term of this patent is extended or adjusted under 35 U.S.C. 154(b) by 420 days.

(21) Appl. No.: 14/561,335

(22) Filed: Dec. 5, 2014

(65) Prior Publication Data

US 2015/0201989 A1    Jul. 23, 2015

Related U.S. Application Data

(62) Division of application No. 12/997,056, filed as application No. PCT/US2009/046989 on Jun. 11, 2009, now Pat. No. 8,906,005.

(60) Provisional application No. 61/060,542, filed on Jun. 11, 2008.

(51) Int. Cl.
  *A61B 18/02*    (2006.01)

(52) U.S. Cl.
  CPC .. *A61B 18/0218* (2013.01); *A61B 2018/0275* (2013.01)

(58) Field of Classification Search
  CPC . A61B 18/02; A61B 18/0206; A61B 18/0218; A61B 2018/0212–2018/0293
  See application file for complete search history.

(56) References Cited

U.S. PATENT DOCUMENTS

| | | |
|---|---|---|
| 4,015,606 A | 4/1977 | Mitchiner et al. |
| 4,082,096 A | 4/1978 | Benson |
| 5,516,505 A | 5/1996 | McDow |
| 5,738,682 A | 4/1998 | Jensma |
| 7,485,117 B2 | 2/2009 | Damasco et al. |
| 7,604,632 B2 | 10/2009 | Howlett et al. |

(Continued)

FOREIGN PATENT DOCUMENTS

| | | |
|---|---|---|
| WO | 2006033905 A1 | 3/2006 |
| WO | 2007005523 A2 | 1/2007 |

OTHER PUBLICATIONS

Supplementary European Search Report of Application No. EP 09763584, dated Jun. 11, 2012.

(Continued)

*Primary Examiner* — Daniel Fowler
(74) *Attorney, Agent, or Firm* — J.A. Lindeman & Co., PLLC

(57) ABSTRACT

A method of preparing a cryo-surgical system for treatment includes accessing a container containing a refrigerant, a delivery tube having a first end configured to be in flow communication with the container and a second end opposite the first end. The system further includes a plurality of flexible finger portions disposed proximate the second end of the delivery tube opposite the first end. A porous applicator bud is disposed proximate the second end of the delivery tube. The porous applicator bud includes a body portion disposed between the plurality of flexible finger portions and a contact surface extending from the plurality of flexible finger portions. An adjustment ring disposed along the delivery tube adjacent to the plurality of flexible finger portions can be used to adjust the size of the contact surface of the porous applicator bud.

13 Claims, 8 Drawing Sheets

(56) References Cited

U.S. PATENT DOCUMENTS

| | | |
|---|---|---|
| 2005/0043723 A1 | 2/2005 | Howlett et al. |
| 2006/0116670 A1 | 6/2006 | Scott et al. |
| 2006/0189968 A1 | 8/2006 | Howlett et al. |
| 2006/0271032 A1 | 11/2006 | Chin et al. |
| 2007/0005048 A1 | 1/2007 | Niedbala et al. |
| 2007/0161975 A1 | 7/2007 | Goulko |
| 2007/0167939 A1 | 7/2007 | Duong et al. |
| 2007/0233054 A1 | 10/2007 | Babaev |
| 2008/0051807 A1 | 2/2008 | St. Goar et al. |
| 2008/0119839 A1 | 5/2008 | Vancelette |
| 2009/0138000 A1 | 5/2009 | Vancelette et al. |
| 2009/0149932 A1 | 6/2009 | Thompson et al. |
| 2009/0209952 A1 | 8/2009 | Van Der Heijden et al. |
| 2009/0248001 A1 | 10/2009 | Burger et al. |
| 2011/0152851 A1 | 6/2011 | Formica |

OTHER PUBLICATIONS

International Search Report of International Application No. PCT/US2009/046989 dated Feb. 3, 2010.
International Preliminary Report on Patentability of International Application No. PCT/US2009/046989 dated Dec. 14, 2010.
Extended European Search Report of EP Application No. 14180657.0 dated Jan. 19, 2015.

CRYO-SURGICAL SYSTEMS AND METHODS OF USING THE SAME

CROSS-REFERENCE TO RELATED APPLICATIONS

This application is a divisional application of U.S. patent application Ser. No. 12/997,056, filed on Mar. 14, 2011, which is a U.S. national phase application of PCT/US2009/046989, filed on Jun. 11, 2009, which claims priority to U.S. Provisional Application No. 61/060,542, filed on Jun. 11, 2008. This application claims the benefit of priority to these previously-filed applications, and the entire contents of these previously-filed applications are incorporated herein by reference.

TECHNICAL FIELD

The present invention relates to a system and method for performing lesion removal, and more particularly, to a cryo-surgical device and method of using a cryo-surgical device that enables removal of lesions having different sizes.

BACKGROUND

Conventional cryo-surgical systems for removing lesions have fixed sized buds. However, different sized buds (i.e. 5 mm and 2 mm) are available to treat various sized lesions. For professional or Over-The-Counter (OTC) applications, the user is never sure how many treatments will be required to remove the lesion, or which sized bud will be needed to effectively treat the lesion. Much of the pain associated with the treatment of lesions results from the freezing of the lesion, as well as the freezing of healthy tissue that surrounds the lesion. Accordingly, matching the size of the bud to the lesion to be treated will minimize the pain associated with the treatment. In addition, due to the viral nature of many lesions, it is recommended that a bud be used for only one treatment location.

There are many factors that determine the number of treatments which will be needed to remove the lesions in both the professional and OTC markets. In the OTC market, the user must purchase a kit where the total number of treatments ranges from 7 to 12, and includes buds and a pressurized can containing a sufficient amount of refrigerant to effectively treat the lesion. Accordingly, the pressurized can with the refrigerant must maintain integrity at high temperatures during the shipping process to retail markets. However, since most OTC kits require a valve to release the refrigerant during each of the separate treatments, the valve must withstand the internal pressures of the can at high temperatures and minimize any leaking of the refrigerant from within the can that could reduce the shelf life of the kit. Accordingly, the pressurized can must have sufficient refrigerant to compensate for any normal losses during shipping, and storage during its shelf life, and still deliver the maximum number of treatments up to and including the last day of the kit's defined shelf life. To insure this, manufacturers overfill the pressurized can with refrigerant and increase the pressure within the can. As a result, after utilizing all of the individual buds provided with the kit for the treatments, any residual pressurized refrigerant remains in the can and presents issues regarding environmentally safe disposal, as well as an explosion hazard for the user during the disposal process.

In light of the above issues, it may therefore be desirable to provide a cryo-surgical system capable of match the bud size to the size of a targeted lesion or area of a lesion. It may further be desirable to adjust the bud size of a treatment system to substantially reduce the damage to healthy tissue adjacent to a targeted lesion or treatment area of a lesion. It also may be desirable to provide a single-use cryo-surgical treatment for lesions. Further it may be desirable to provide a system having a configuration to provide for precise treatment of lesions in substantially hard to reach locations.

SUMMARY

The present teachings may solve one or more of the above-mentioned problems. Other features and/or advantages may become apparent from the description which follows.

In various exemplary embodiments, the present teachings contemplate a cryo-surgical system comprising a container containing a refrigerant; a delivery tube having a first end configured to be in flow communication with the container and a second end opposite the first end; a plurality of flexible finger portions disposed proximate a second end of the delivery tube opposite the first end; an applicator bud having a body portion disposed within the plurality of flexible finger portions and a contact surface extending from the plurality of flexible finger portions; and an adjustment ring disposed along the delivery tube adjacent to the plurality of flexible finger portions. The contact surface of the bud may be changeable by adjustment of the adjustment ring.

In various exemplary embodiments, the present teachings also contemplate a method of treating a lesion, the method comprising providing a container containing a refrigerant and a delivery tube having a first end configured to be in flow communication with the container and a second end opposite the first end, and an applicator bud disposed proximate the second end; adjusting a size of the applicator bud by compressing a surface of the applicator bud; delivering refrigerant from the container to the applicator bud; and applying the applicator bud to a targeted treatment lesion area to freeze the lesion area.

Additional objects and advantages may be set forth in part in the description which follows, and in part will be obvious from the description, or may be learned by practice of the present teachings. Those objects and advantages will be realized and attained by means of the elements and combinations particularly pointed out in the appended claims.

It is to be understood that both the foregoing general description and the following detailed description are exemplary and explanatory only and are not restrictive of the present teachings or claims.

DETAILED DESCRIPTION OF VARIOUS EXEMPLARY EMBODIMENTS

Figure 1:
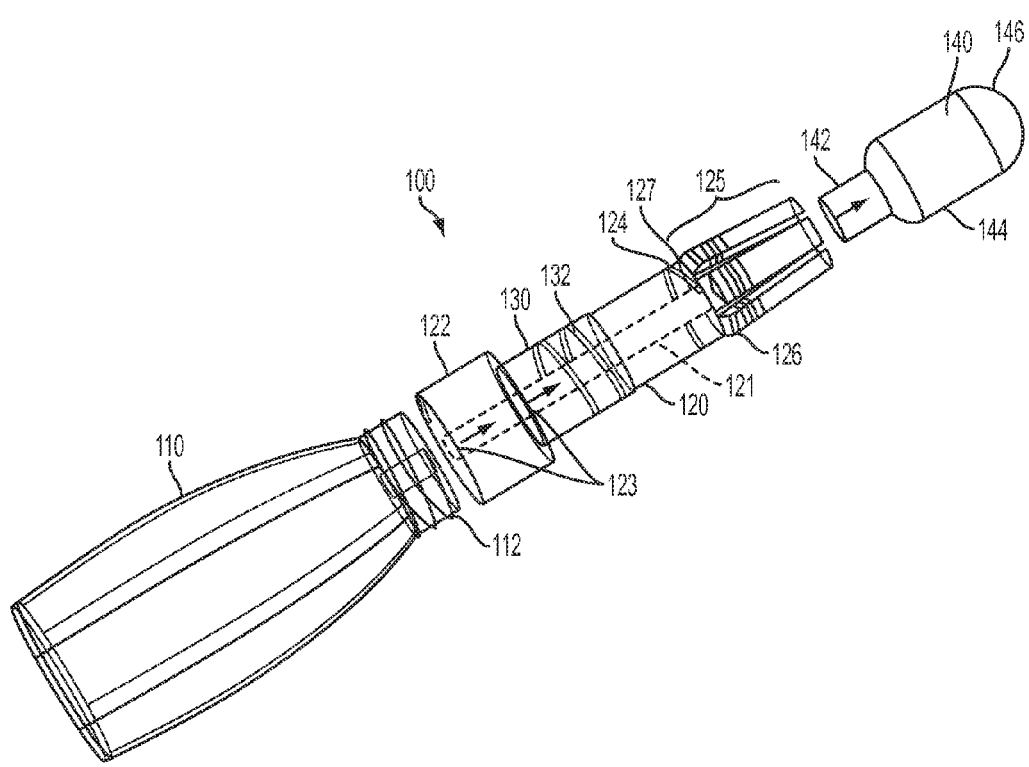
FIG. 1 is a perspective assembly view with some internal components shown of an exemplary cryo-surgical system according to the present invention.

FIG. 1 is a perspective assembly view of an exemplary cryo-surgical system according to the present invention. In FIG. 1, a cryo-surgical system 100 includes a container 110 having an opening portion 112, a delivery tube 120 having a first end 122 configured to be connected to the container 110, an adjustment ring 130 slideably disposed on the delivery tube 120, and a bud 140 coupled within a second end 124 of the delivery tube 120. The opening portion 112 of the container 110 may have external threads that engage internal threads of the first end 122 of the delivery tube 120. In an exemplary embodiment, the container 110 may be configured to contain enough refrigerant for a single-use treatment, wherein the amount of refrigerant for the single-use treatment is dependent upon the size, configuration, and material of the bud 140 in order to establish a treatment temperature of the bud 140 to be approximately at least about −27° C., and preferably lower than about −27° C. For example, the container 110 may contain from about 3 ml to about 4 ml of refrigerant, which may or may not be under substantial pressure. Accordingly, in the exemplary embodiment of FIGS. 1 and 2, no valve is required between the container 110 or the delivery tube 120, thereby reducing costs and maintaining a safe way to provide treatment of a lesion. Although the container 110 is shown having a substantially flask-type configuration, the container 110 may include other shapes to improve usefulness by the user.

Although not specifically shown, the first end 122 may include a protrusion to pierce or rupture a sealed surface of the opening portion 112 of the container 110. For example, by coupling together the container 110 and the delivery tube 120 using the threaded opening portion 112 and the first end 122, the protrusion may puncture the sealed surface of the opening portion 112 of the container 110, thereby establishing a fluid connection between the refrigerant within the container 110 and the delivery tube 120, and hence the bud 140. Accordingly, there is no valve system or device required or needed between the delivery tube 120 and the container 110 to regulate the flow of refrigerant. However, in some exemplary embodiments, in particular depending on the type of refrigerant, such as, for example, high pressure, flammable refrigerants, in the container 110, a valving mechanism may be desirable to and thus the exemplary embodiment without a valve is non-limiting and exemplary only.

Figure 2:
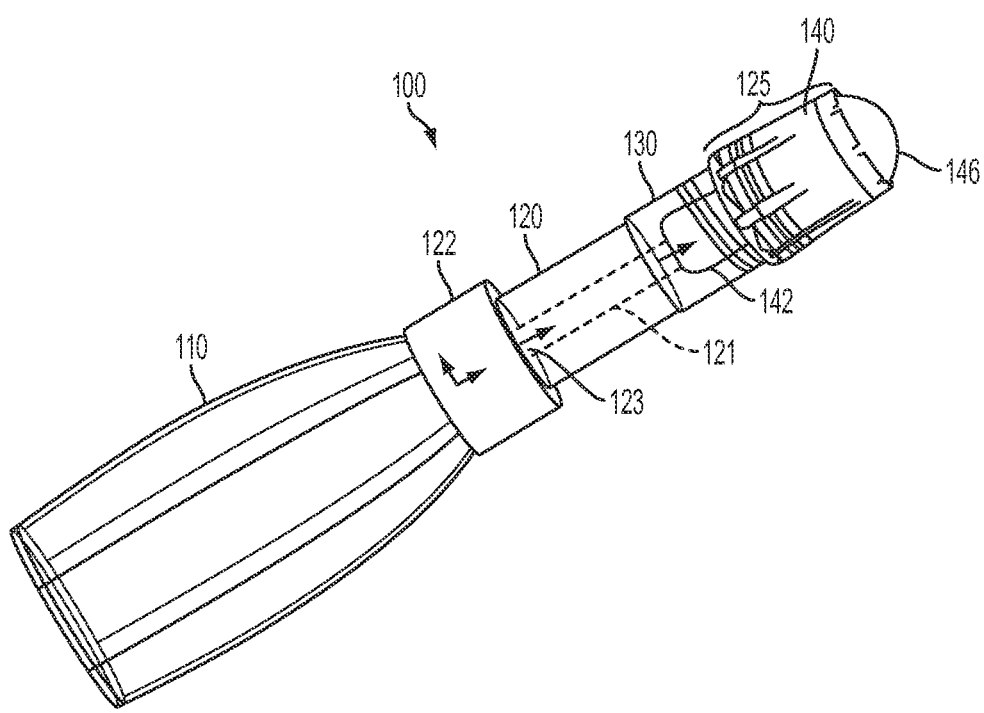
FIG. 2 is a perspective view, showing some internal features of the exemplary cryo-surgical system of FIG. 1 according to the present invention.

In the exemplary embodiment of FIGS. 1 and 2, the delivery tube 120 may define a delivery lumen 121 (shown in dashed lines in FIGS. 1 and 2) having openings 123, 127 at opposite ends to flow the refrigerant from the container 110 through the delivery tube 120 and to the bud 140. In an exemplary embodiment, the lumen 121 may have a cross-section that is smaller than the outer cross-section of the delivery tube 120. However, in alternative configurations, the delivery tube outer cross-section may be approximately the same size as the cross-section of the delivery lumen. Such an alternative configuration is depicted in the exemplary embodiment of FIGS. 5-7, described in further detail below.

Figure 3A:
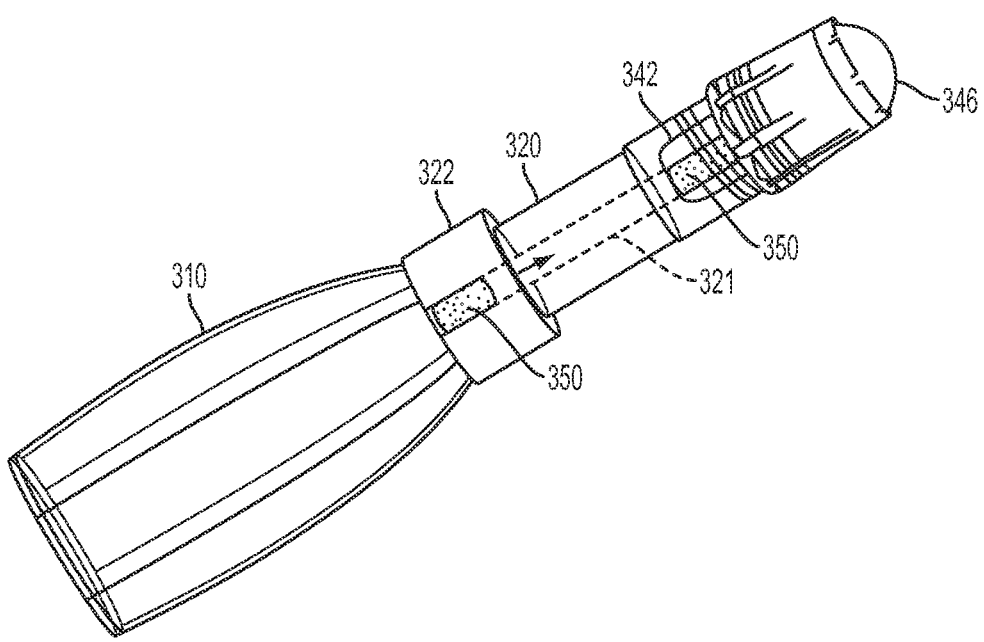
FIGS. 3A-3C are perspective views, showing some internal features, of other exemplary cryo-surgical systems in accordance with the present invention.
Figure 3B:
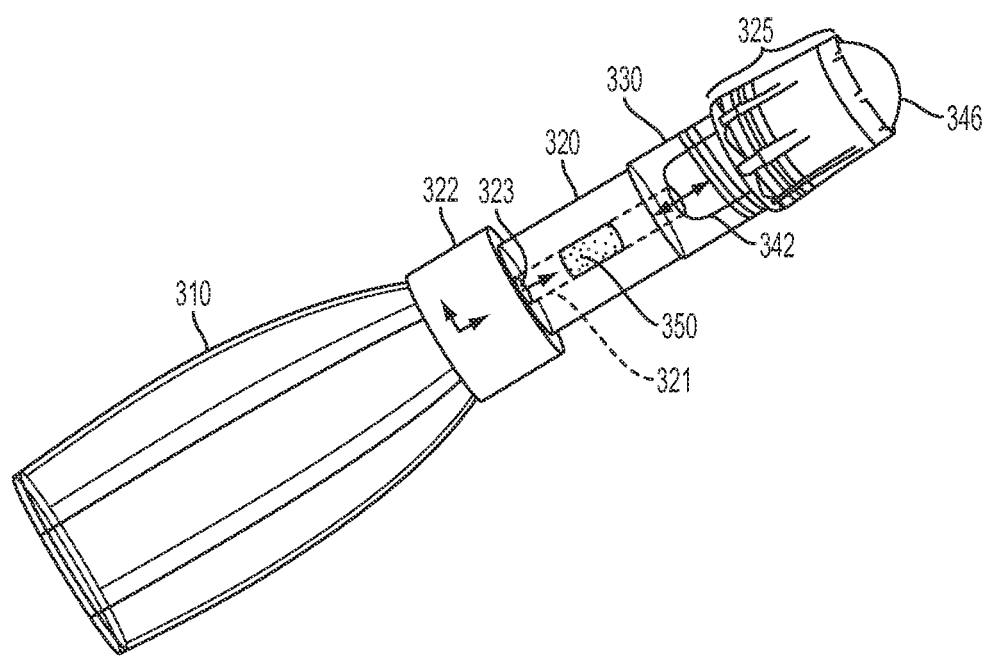
Figure 3C:
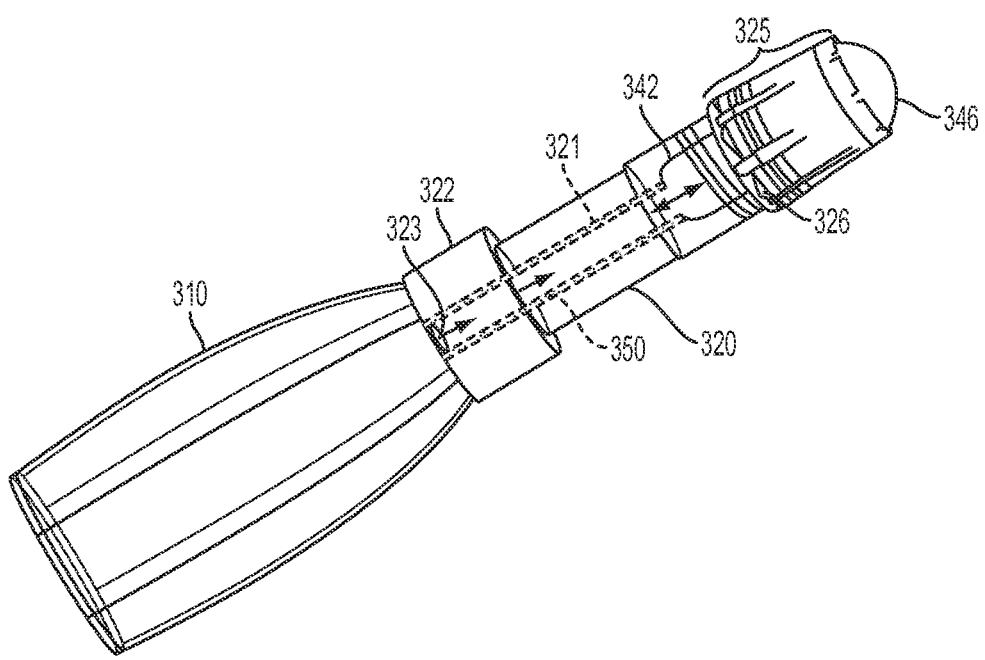

In another exemplary embodiment, the delivery tube 120 may contain porous material or materials to transmit the refrigerant from the container 110 to the bud 140. Accordingly, the porous material(s) within the delivery tube 120 may be the same or different from the material(s) that form the bud 140, as detailed below. Moreover, the porous material(s) may be provided along only a portion or portions of the delivery tube 120. For example, as depicted in the exemplary embodiment of FIG. 3A, the porous material(s) 350 may be provided within the lumen 321 at the first and second ends 322 and 324 with a middle portion of the delivery tube 320 void of any porous material(s). In the exemplary embodiments of FIGS. 3A-3B, the various parts of the systems are the same as are shown and described for the exemplary embodiment of FIGS. 1-2, but have been labeled with a 300 series of reference numerals. Alternatively, as depicted in FIG. 3B, only a middle portion of the lumen 321 of the delivery tube 320 may include porous material(s) 350. Those having ordinary skill in the art will appreciate that various combinations of the placement of porous materials 350 are considered within the scope of the present teachings, for example, porous material 350 may fill the entire lumen 321. In another exemplary embodiment, depicted in FIG. 3C, the porous material(s) 350 may be provided as a hollow tube concentrically disposed within the lumen 321 of the delivery tube 320 such that a hollow pathway may be provided along a length of the delivery tube 320 from the container 310 to the bud 340. In FIGS. 3A-3C, other components of the cryo-surgical systems are the same as those shown and as described herein with reference to FIGS. 1 and 2 and therefore are not specifically described herein.

In exemplary embodiments wherein porous material(s) fill a delivery lumen or are otherwise in contact with the applicator bud, the porous material(s), act as a reservoir to receive the refrigerant and to supply the bud with refrigerant. As the refrigerant evaporates from the bud, additional refrigerant is supplied from the porous material. In this manner, a wicking effect is created whereby the porous material feeds the bud with additional refrigerant as refrigerant from the outer surface of the bud evaporates. The refrigerant received and held by the porous material is predominantly, if not completely, in the liquid state. Supplying additional liquid refrigerant to the bud allows the bud to maintain its cold temperature for a longer period of time. This increases the depth and efficacy of freezing and, therefore, the cryosurgical treatment. This can be particularly useful for single-use cryosurgical devices. For a single-use cryosurgical device, the refrigerant can be discharged and increased duration of treatment may be achieved with exemplary embodiments including porous materials in conjunction with a bud.

Exemplary refrigerants used in accordance with the present invention preferably have a boiling point at atmospheric pressure within a range from about 25° C. to about −120° C., for example from about 0° C. to about −75° C. Suitable refrigerants may include, but are not limited to, halogenated hydrocarbons (i.e., tetrafluoromethane, trifluoromethane, monochlorotrifluoromethane, hexafluoroethane, monobromotrifluoromethane, monochlorodifluoromethane, monochloropentafluorothane, dichlorodifluoromethane, 1,2-dichloro-1,1,2,2-tetrafluoroethane, trichloromonofluoromethane, 1,1,2-trichloro-1,2,2-trifluoromethane and 1,1-difluoroethane), propane, n-butane, isobutane, dimethyl ether, and nitrogen. Dimethyl ether and alkanes, such as propane, are preferable for environmental reasons.

With reference again to FIG. 1, the bud 140 includes a first end portion 142 that insertably receives the delivery tube 120, a body portion 144 disposed within the second end 124 of the delivery tube 120, and a second end portion 146 to extend from the second end 124 of the delivery tube 120. Here, the body portion 144 will be frictionally retained by the delivery tube 120. For example, the delivery tube 120 may comprise finger portions 125 that flexibly fit around the body portion 144. The finger portions 125 may be flexible to permit substantially elastic movement of the finger portions 125 inwardly and outwardly (i.e., toward and away from the bud 140). The contact surface of the second end portion 146 may have a maximum, uncompressed diameter of about 5 mm, but may be increased or reduced based upon the size of the lesion to be treated.

The bud 140 is formed of a porous material or materials. For example, the bud 140 is composed of cotton wool, open-celled foams, and polyolefin or polyester non-woven fabrics. Here, the material(s) of the bud 140 do not react chemically with the refrigerant and has suitable physical properties throughout the range of temperatures to which the bud 140 is exposed during use, for example, from about 25° C. to about −120° C.

The density of the material(s) is preferably less than about 60 kg/m3, and preferably within a range of about 10 kg/m3 to about 40 kg/m3, and more preferably within a range of about 12 kg/m3 to about 35 kg/m3, and even more preferably within a range of about 26 kg/m3 to about 32 kg/m3. The pore size of the bud 140 is preferably within a range of about 5 pores/cm to about 50 pores/cm, and preferably within a range of about 20 pores/cm to about 40 pores/cm, and more preferably within a range of about 30 pores/cm to about 40 pores/cm, and even more preferably within a range of about 27 pores/cm to about 32 pores/cm.

The bud 140 may be formed from suitable foam-type polymer material(s) including, but not limited to, polyesters, polyethers, polyurethanes, polyethylene, polypropylene, phenolic resins, polystyrenes and polyvinyl chloride resins, and in particular, polyester-based polyurethanes. Preferably, the foam-type material(s) is composed of a polymer that is wettable by the refrigerant, thereby quickly obtaining lower treatment temperatures and/or increased effective treatment times. Open-celled foam materials are preferred.

The bud 140 also may comprise layers of porous materials, for example, layers of differing porous materials.

According to an embodiment of the present invention, the bud 140 may also include an internal cavity. When the refrigerant is provided to the bud 140, the foam material(s) is subject to internal pressure from the refrigerant and may be subject to external pressure when pressed against the targeted treatment area of the lesion. Accordingly, the wall thickness of the bud 140 should be selected accordingly. In addition, the cavity may be filled, at least in part if not entirely, with a suitable permeable and absorbent solid material or materials. The material(s) modifies and controls the pressure and flow of the refrigerant into the interior cavity of the bud 140 so that the cooling effect is more uniform and more reproducible. For example, cotton wool may be placed within the cavity of the bud 140 due to its permeability and absorbency. In addition, other materials, including other non-woven fibrous cellulosic or non-cellulosic materials could also be used. The presence of the cotton wool or other permeable material can also improve the physical strength of the bud 140. The cotton wool or other material(s) provided within the cavity of the bud 140 may fill the cavity in order to make direct contact with the walls of the cavity, thereby providing physical support to the bud 140. This type of bud is described in Jensma, U.S. Pat. No. 6,387,090, which is incorporated by reference herein.

Although not specifically shown, the bud 140 and/or the plurality of finger portions 125 may also include a protective wrapper or cover to maintain integrity of the system 100. Accordingly, prior to using the system 100, the user may remove the wrapper before attaching the delivery tube 120 to the container 110.

FIG. 2 is a perspective view of the exemplary cryosurgical system of FIG. 1 according to the present invention. In FIG. 2, the adjustment ring 130 is positioned toward the second end 124 of the delivery tube 120. Here, the adjustment ring 130 includes an internal threaded portion 132 which engages external threads of the second end 126 of the delivery tube 120. Since the inner diameter of the adjustment ring 130 is smaller than the outer diameter of the delivery tube 120, the adjustment ring 130 may be slid into position with respect to the finger portions 125. As the adjustment ring 130 is tightened along the external threads of the second end 126 of the delivery tube 120, the adjustment ring 130 travels toward the finger portions 125. Accordingly, the adjustment ring 130 causes the finger portions 125 to close around the body portion 144 and second end portion 146 of the bud 140, thereby compressing the body portion 144 and the second end portion 146 and reducing a contact surface of the second end portion 146 of the bud 140. Thus, the contact surface 146 may be reduced using the adjustment ring 130 to treat a relatively small targeted treatment area of a lesion. Conversely, the contact surface of the second end portion 146 of the bud 140 may be maximized by merely tightening the adjustment ring 130 snuggly so as to not compress the bud 140 using the finger portions 125 in order to treat a larger targeted lesion or treatment area of a lesion. As a result, the bud 140 may be adjusted to provide for treatment of relatively large and small targeted lesion or treatment areas of a lesion by tightening or loosening the adjustment ring 130.

Alternatively, the adjustment ring 130 may be frictionally fit to the finger portions 125 such that the internal threads 132 of the adjustment ring 130 and the external threads at the second end 126 of the delivery tube 120 are not necessary in order to compress the bud 140.

Figure 4:
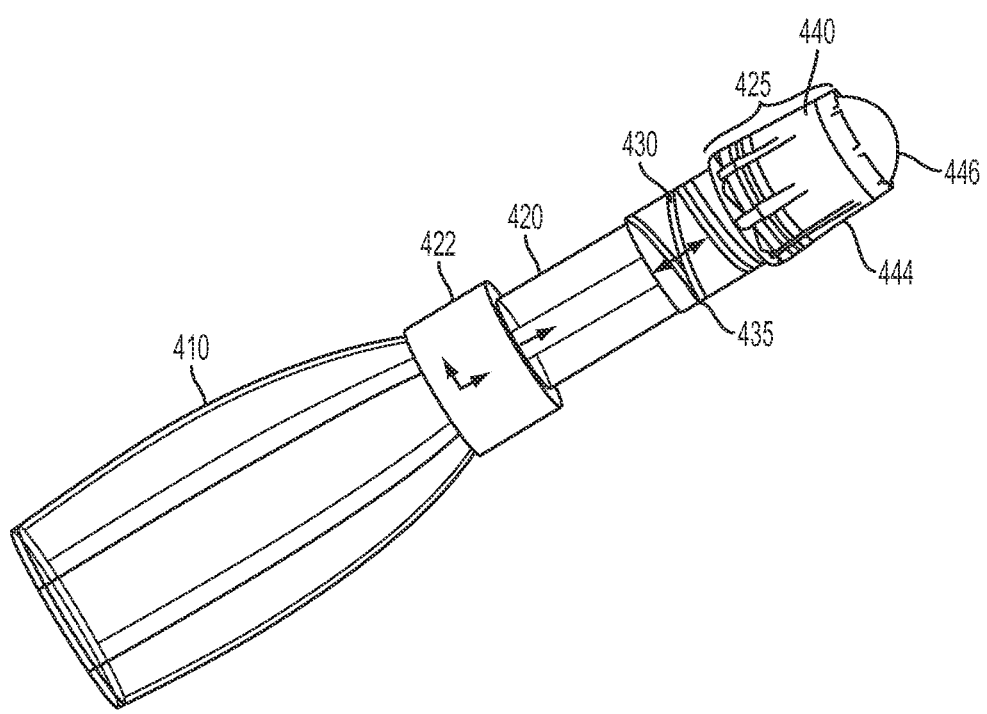
FIG. 4 is a perspective view, showing some internal features, of yet another exemplary cryo-surgical system in accordance with the present invention.

In another exemplary embodiment, illustrated in FIG. 4, an adjustment ring 430 having a configuration similar to adjustment ring 130 may be attached to the upper end 424 of the delivery tube 420 proximate finger portions 425. The adjustment ring 430 may be attached to the delivery tube 420 via a spring 435 (shown underneath the adjustment ring 430 in FIG. 4). When it is desired to increase the size of the bud 440, the adjustment ring 430 may be moved in a direction toward the container 410, thereby compressing the spring 435 toward the container and permitting the adjustment fingers 425 to open outwardly, at least partially removing the compression forces from the body portion 444 and second end portion 446 of the bud 440. When it is desired to decrease the size of the bud 440, the adjustment ring 430 may be moved in a direction toward the bud 440, thereby compressing spring 435 and engaging the adjustment ring 430 with the finger portions 425. This will cause the finger portions 425 to close around the body portion 444 and potentially some of the second end portion 446 of the bud 440, thereby compressing the body portion 444 and the second end portion 446 and reducing a contact surface of the second end portion 446 of the bud 440. In another exemplary configuration, the adjustment ring 430 may be either spring-biased in a direction so as to be in engagement with the finger portions 425 so as to compress the bud 440 and if a larger bud size is desired, the adjustment ring 430 may be moved toward the container 410 to release the finger portions 425 to the extent desired. In yet another exemplary configuration, the adjustment ring 430 may be spring-biased toward the container 410 and out of engagement with the finger portions 425 so as to render the bud 440 in an uncompressed, larger configuration, and if desired, the adjustment ring 430 may be moved into engagement with the adjustment fingers 425 by compressing the spring 435 to compress the bud 440. Aside from the operability and configuration of the adjustment ring, remaining components of the cryo-surgical system of FIG. 4 are the same as those shown and as described herein with reference to FIGS. 1 and 2 and therefore are not specifically described herein.

According to the present invention, the exemplary cryo-surgical systems described herein may also include a plurality of different sized buds to provide the user with improved flexibility for treating a substantially large range of targeted lesions or treatment areas of lesions. Here, the user may select the appropriate size bud based upon the approximate size of the lesion of targeted treatment area of the lesion.

In addition, the exemplary cryo-surgical system 100 may also include different sized buds to provide with individual delivery tubes 120 to further provide the user with improved flexibility for treating a substantially large range of targeted lesions or treatment areas of lesions. Here, the user may select the appropriate delivery tube 120 having the specific size bud based upon the approximate size of the targeted lesion or treatment area of the lesion. Similarly, the contact surface of the second end portion 146 of the bud 140 may have different geometrical configurations, such as conical, chisel, or cylindrical geometries.

Furthermore, the delivery tube 120 may be formed not only as a linear cylindrical tube, but may include a curved offset portion or portions to provide the user with the ability to treat hard-to-reach lesion locations, such as the back, lower leg, shoulder, etc. For example, the delivery tube 120 may have a first portion extending along a first direction from the container 110 and a second portion or portions extending along a second direction at an angle from the first direction. Moreover, the delivery tube 120 may have a U-shaped or J-shaped configuration. In addition, the delivery tube 120 may be formed having flexible portions, or flexible along an entire length of the delivery tube 120, to allow the user to shape the delivery tube 120 for easy treatment of lesion locations.

According to the present invention, the bud 140 may be formed of various materials that provide for absorption and flow of the refrigerant from the container 110. Here, the bud 140 may be formed of a single material, or may be formed of multiple materials, as detailed above. For example, the first end portion 142, the body portion 144 and the contact surface of the second end portion 146 may be formed of a single-density foam. Alternatively, the first end portion 142 may be formed of a first density foam, the body portion 144 may be formed of a second density foam, and the contact surface of the second end portion 146 may be formed of a third density foam, wherein each of the first, second, and third densities may be substantially different. Moreover, the first end portion 142 may be formed of a first density foam, and the body portion 144 and the contact surface of the second end portion 146 may be formed of a second density foam, wherein the first and densities may be substantially different. These configurations may also apply to buds of the other exemplary embodiments shown and described herein.

According to the present invention, treatment of a lesion is not limited to lesions located on exterior surfaces of the body. Specifically, the present invention may be used to treat lesions in cavities in the body. Accordingly, an overall length of the delivery tube 120 may be adjusted using an extendible coupling or mechanism to treat lesions or tissues deep inside the human body. Here, the flow of the refrigerant from the container 110 may need to be initiated after the bud 140 is positioned against the lesion or tissue to be treated in order to prevent damaging healthy tissue disposed along the pathway between the lesion or tissue to be treated and the point of entry into the cavity of the delivery tube 120. For, the flow of refrigerant from the container 110 may be commenced once the contact surface of the second end portion 146 of the bud 140 is in proper position to treat the lesion or tissue. Here, a rupturing mechanism (not shown) may be incorporated into the first end portion 122 of the delivery tube 120 to allow the user to initiate flow of the refrigerant from within the container 110, through the delivery tube 120, and through the bud 140 to the contact surface of the second end portion 146 after positioning the bud 140 against the lesion or tissue to be treated. As above, such configurations may apply to the exemplary embodiments and corresponding components of other of the exemplary embodiments shown and described herein.

Figure 5:
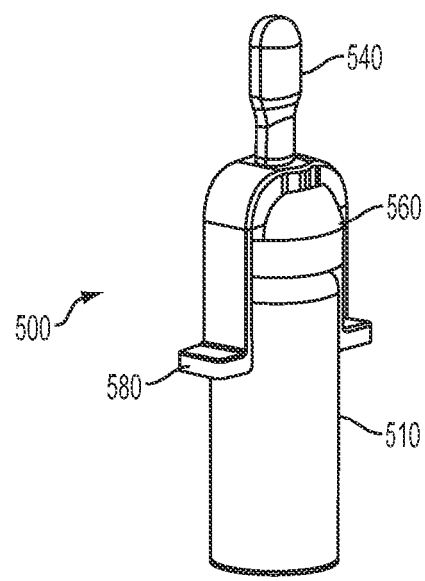
FIG. 5 is a perspective view of yet another exemplary cryo-surgical system in accordance with the present invention.
Figure 6:
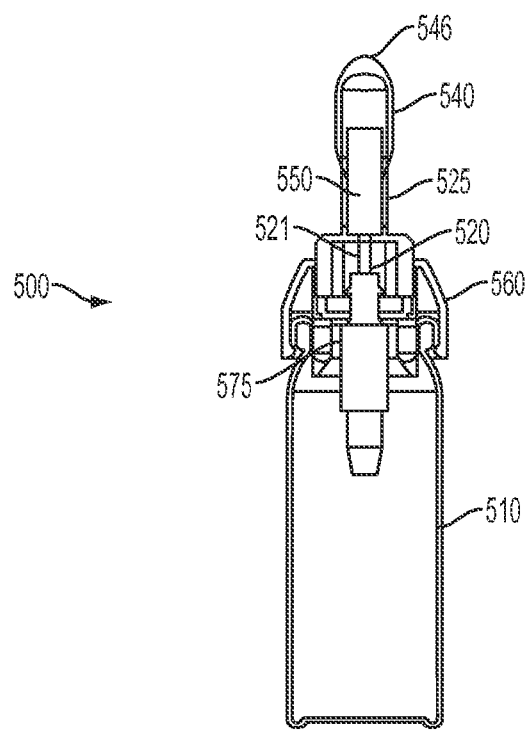
FIG. 6 is a cross-sectional view of the cryo-surgical system of FIG. 5.

Although various exemplary embodiments of the present teachings have been described as not including a valving mechanism, those having ordinary skill in the art will appreciate that a valving mechanism may be used if desired with any of the exemplary embodiments of FIGS. 1-4, and may be desirable in situations where a high pressure, flammable refrigerant in used. FIGS. 5 and 6 depict another exemplary embodiment of a cryosurgical system 500 that utilizes a valving mechanism 575 to permit or stop the flow of the refrigerant from a container 510 containing the refrigerant to a delivery tube 520 defining a delivery lumen 521 and ultimately to a bud 540. With reference to the perspective view of FIG. 5, the device 500 may be provided with an actuation mechanism 580 configured to be pulled or depressed toward an end of the device 500 opposite the bud 540 to place the valving mechanism 575 in an open position to permit flow of the refrigerant from the container 510 through the valving mechanism 575 and into the delivery lumen 521. The valving mechanism 575 may be any type of conventional valving mechanisms configured to provide such flow control with which those ordinarily skilled in the art have familiarity. In one exemplary configuration, the actuation member 580 may be locked into the depressed position. However, other configurations contemplate that the actuation member 580 may be spring-biased toward the position closing the valving mechanism 575 and operated in a manner similar to a trigger-type of valve mechanism on other known containers for dispensing fluids, for example, by a user having to continually apply force to the actuation member 580 to maintain the actuation member 580 in the position that opens the valving mechanism 575.

Those having skill in the art will also appreciate that in the exemplary embodiment depicted in FIG. 6, to dispense the fluid from the container 510, the container 510 needs to be inverted. However, as those ordinarily skilled in the art will appreciate, a dip tube could be provided from the end of the valving mechanism and extending into the container if dispensing of the refrigerant is desired while leaving the container 510 in a non-inverted position (i.e., in the position depicted in FIGS. 5 and 6).

As shown in FIG. 6, the delivery tube 520 may open up into a tube 525 of larger outer and internal dimensions and that is filled with porous material(s) 550. The porous material(s) 550 may be used in the manner described for the porous materials 350 described above with reference to the exemplary embodiments of FIGS. 3A-3C, that is, to store and flow refrigerant to the bud 540 (e.g., via a wicking type of effect) as refrigerant evaporates from the bud 540.

Figure 7:
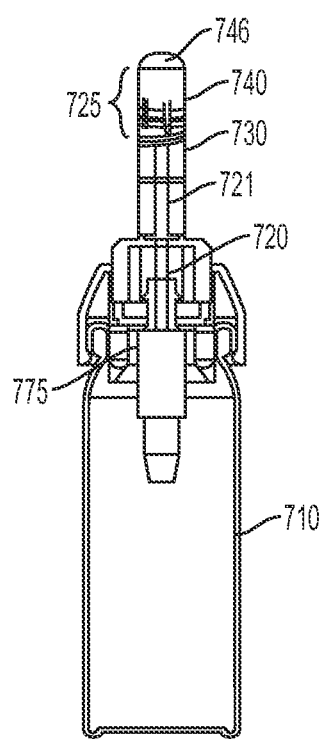
FIG. 7 is a cross-sectional view of another exemplary embodiment of a cryo-surgical system in accordance with the present invention.

Referring now to FIG. 7, another exemplary embodiment of a cryosurgical system 700 is depicted. The system 700 has a similar configuration to that of FIGS. 5 and 6, (with like parts being labeled with like reference numerals except with a 700 series), with the exception that the system 700 includes adjustable finger portions 725 and an adjustment ring 730 that may operate and have a configuration similar to that described with reference to the exemplary embodiments of FIGS. 1, 2 and 4 to adjust the size of the bud 740 and second end portion 746.

The exemplary embodiments of FIGS. 5-7, like those of FIGS. 1-4, can be configured as single-use devices. In various exemplary embodiments, the containers 510 and 710 may define a volume configured to hold enough refrigerant to deliver an amount of refrigerant to sufficiently freeze a skin lesion or perform the desired cryo-surgical treatment over a desired time period. For example, the containers 510 and 710 may be configured to contain enough refrigerant for a single-use treatment, wherein the amount of refrigerant for the single-use treatment is dependent upon the size, configuration, and material of the bud 540, 740 in order to establish a treatment temperature of the bud 540, 740 to be approximately at least about −27° C., and preferably lower than about −27° C. Depending on the type of refrigerant that is being dispensed, it may be desirable to use a system that includes a valving mechanism.

Although the present invention has been described in relation to particular embodiments thereof, many other variations and modifications and other uses will become apparent to those skilled in the art. Those having ordinary skill in the art will understand that various modifications can be made to sizes, materials, arrangements, and types of parts without departing from the scope of the present teachings. Moreover, although some features described herein may have been described in the context of a particular exemplary embodiment, those ordinarily skilled in the art will appreciate that various features of different exemplary embodiments may be combined with other exemplary embodiments. It is intended therefore, that the present teachings be limited not by the specific disclosure herein and that the claims be entitled to their full scope, including equivalents.

What is claimed is:

1. A method of preparing a cryo-surgical system, the method comprising:
   accessing a container containing a refrigerant and a delivery tube having a first end configured to be in flow communication with the container and a second end opposite the first end and including a plurality of flexible finger portions disposed proximate the second end of the delivery tube opposite the first end;
   providing a porous applicator bud disposed proximate the second end of the delivery tube, the porous applicator bud having a body portion disposed between the plurality of flexible finger portions and a contact surface extending from the plurality of flexible finger portions; and
   adjusting a size of the porous applicator bud by at least partially removing compression forces from the porous applicator bud to increase the size of a contact surface of the porous applicator bud or engaging the plurality of flexible finger portions and thereby compressing the contact surface of the porous applicator bud.

2. A method of claim 1 further comprising:
   delivering refrigerant from the container to the porous applicator bud; and
   applying the porous applicator bud to a targeted treatment lesion area to freeze the lesion area.

3. A method according to claim 1, wherein delivering the refrigerant from the container to the porous applicator bud includes flowing the refrigerant from the container to the porous applicator bud via the delivery tube.

4. A method according to claim 1, wherein delivering the refrigerant from the container to the porous applicator bud includes delivering the refrigerant from the container to the porous applicator bud without using a valving mechanism.

5. A method according to claim 1, wherein delivering the refrigerant from the container to the porous applicator bud includes storing the refrigerant from the container in a porous material and supplying the stored refrigerant from the porous material to the porous applicator bud.

6. A method according to claim 1, further comprising:
   coupling the delivery tube to the container to place a lumen of the delivery tube in flow communication with the refrigerant in the container.

7. A method according to claim 6, wherein coupling the delivery tube to the container includes penetrating a sealing member on the container.

8. A method according to claim 1 further comprising:
   coupling the first end of the delivery tube directly to the container without an intervening valve device therebetween.

9. A method according to claim 1, wherein adjusting the size of the porous applicator bud includes engaging an adjustment ring with the plurality of flexible finger portions.

10. A method according to claim 9, wherein the adjustment ring is disposed along the delivery tube adjacent to the plurality of flexible finger portions.

11. A method of claim 9, wherein engaging the adjustment ring includes loosening the adjustment ring to at least partially remove compression forces from the porous applicator bud to increase the size of the contact surface of the porous applicator bud or tightening the adjustment ring to compress the contact surface of the porous applicator bud.

12. A method according to claim 9, wherein engaging the adjustment ring with the plurality of flexible finger portions includes engaging a threaded portion of the adjustment ring with a threaded portion of the delivery tube.

13. A method according to claim 9, wherein the adjustment ring is engaged by a spring-biased movement relative to the plurality of flexible finger portions.

* * * * *